United States Patent [19]
Beecher et al.

[11] Patent Number: 6,083,697
[45] Date of Patent: Jul. 4, 2000

[54] CHEMICAL AMPLIFICATION FOR THE SYNTHESIS OF PATTERNED ARRAYS

[75] Inventors: Jody E. Beecher, Mountain View; Martin J. Goldberg, San Jose; Glenn H. McGall, Mountain View, all of Calif.

[73] Assignee: Affymetrix, Inc., Santa Clara, Calif.

[21] Appl. No.: 08/969,227

[22] Filed: Nov. 13, 1997

Related U.S. Application Data

[60] Provisional application No. 60/030,826, Nov. 14, 1996.

[51] Int. Cl.$^7$ .............................. C12Q 1/68; G01N 33/53; G03C 5/00; G03C 1/76
[52] U.S. Cl. ................................ 435/6; 435/7.1; 422/134; 422/129; 430/8; 430/269; 430/270.1; 430/311
[58] Field of Search ........................ 435/7.1, 6; 422/134, 422/129; 430/269, 270.1, 311

[56] References Cited

U.S. PATENT DOCUMENTS

| | | |
|---|---|---|
| 4,189,323 | 2/1980 | Buhr . |
| 4,442,197 | 4/1984 | Crivello et al. . |
| 4,603,101 | 7/1986 | Crivello . |
| 4,624,912 | 11/1986 | Zweifel et al. . |
| 4,728,502 | 3/1988 | Hamill . |
| 5,143,854 | 9/1992 | Pirrung et al. . |
| 5,242,974 | 9/1993 | Holmes ................................ 525/54.11 |
| 5,527,681 | 6/1996 | Holmes . |
| 5,679,773 | 10/1997 | Holmes ................................ 530/334 |
| 5,700,637 | 12/1997 | Southern . |

FOREIGN PATENT DOCUMENTS

| | | | |
|---|---|---|---|
| WO 89/10977 | 11/1989 | WIPO .............................. | C12Q 1/68 |
| 90/05746 | 5/1990 | WIPO . | |
| 90/05749 | 5/1990 | WIPO . | |
| 90/05785 | 5/1990 | WIPO . | |
| 90/10977 | 9/1990 | WIPO . | |
| 92/10092 | 6/1992 | WIPO . | |
| 95/11995 | 5/1995 | WIPO . | |
| 96/28457 | 9/1996 | WIPO . | |
| 97/10365 | 3/1997 | WIPO . | |

OTHER PUBLICATIONS

Beecher et al., (1997), Chemically Amplified Photolithography for the Fabrication of High Density Oligonucleotide Arrays, *Polymeric Materials Science and Engineering*, 76: 597–598.

Fodor, et al., (1991), Light–directed, Spatially Addressable Parallel Chemical Synthesis, *Science*, 251:767–773.

Frank and Döring, (1988), Simultaneous Multiple Peptide Synthesis Under Continuous Flow Conditions On Cellulose Paper Discs As Segmental Solid Supports, *Tetrahedron* 44:(19)6031–6040.

Geysen, et al., (1987), Strategies For Epitope Analysis Using Peptide Synthesis, *Journal of Immunological Methods*, 102:259–274.

Ghandi, (1983), Lithographic Processes in *VLSI Fabrication; Silicon and Gallium Arsenide*, Ch. 10;535–565, John Wiley & Sons, New York.

Houlihan, et al., (1991), Design, Synthesis, Characterization, and Use of All–Organic Nonionic Photogenerators of Acid, *Chem. Mater.*, 3:462–471.

Ichimura, et al., (1995), A Novel Concept of Acid Proliferation; Autocatalytic Fragmentation of an Acetoacetate Derivative as an Acid Amplifier, *Chemistry Letters*:551–552.

Kozal, et al., (1996), Extensive Polymorphisms Observed In Hiv–1 clade B Protease Gene Using High–density Oligonucleotide Arrays, *Nature Medicine*, 2(7):753–759.

Kosar (1965), Light–Sensitive Systems: Chemistry and Application of Nonsilver Halide Photographic Processes In *Wiley Series on Photographic Science and Technology and the Graphic Arts*, pp. 342–353, John Wiley & Sons, New York.

Kudo, et al., (1996), Autocatalytic Decomposition of a β–tosyloxy–ketone Acetal As An Acid Amplifier, *Mol Cryst. Liq. Cryst*, 280:307–312.

Merrifield, (1963), Solid Phase Peptide Synthesis. I. The Synthesis of a Tetrapeptide, *Am. Chem. Soc.*, 85:2149–2154.

Onishi, et al., (1991), Acid catalyzed resist for KrF Excimer Laser Lithography, *Journal of Photopolymer Science and Technology*, 4(3):337–340.

Pappas (1985), Photogeneration of Acid: Part 6—A Review of Basic Principles for Resist Imaging Applications, *J.Imaging Technology*:146–157.

Reiser (1989), The Rudiments of Imaging Science In *Photocreative Polymers; the Science and Technology of Resists*, Ch. 6:226–229, John Wiley & Sons, New York.

Thompson, et al., (Eds), (1994), Chemical Amplification In *Introduction to Microlithography*, 2nd Ed., Ch. 3:212–233, American Chemical Society, Washington, D.C.

Stryer, (1995), *Biochemistry*, Chapter 2, pp. 20–23, W.H. Freeman &Co.

Wallraft et al., (1997), DNA sequencing on a chip *CHEMTECH* 27:22–32.

Mac Donald et al, Chemical amplification inhigh–Resolution Imaging Systems, vol. 37 (6) 151–157, Jun. 1994.

*Primary Examiner*—Bennett Celsa
*Assistant Examiner*—Joseph W. Ricigliano
*Attorney, Agent, or Firm*—Banner & Witcoff, Ltd.

[57] ABSTRACT

Radiation-activated catalysts (RACs), autocatalytic reactions, and protective groups are employed to achieve a highly sensitive, high resolution, radiation directed combinatorial synthesis of pattern arrays of diverse polymers. When irradiated, RACs produce catalysts that can react with enhancers, such as those involved in autocatalytic reactions. The autocatalytic reactions produce at least one product that removes protecting groups from synthesis intermediates. This invention has a wide variety of applications and is particularly useful for the solid phase combinatorial synthesis of polymers.

18 Claims, 7 Drawing Sheets

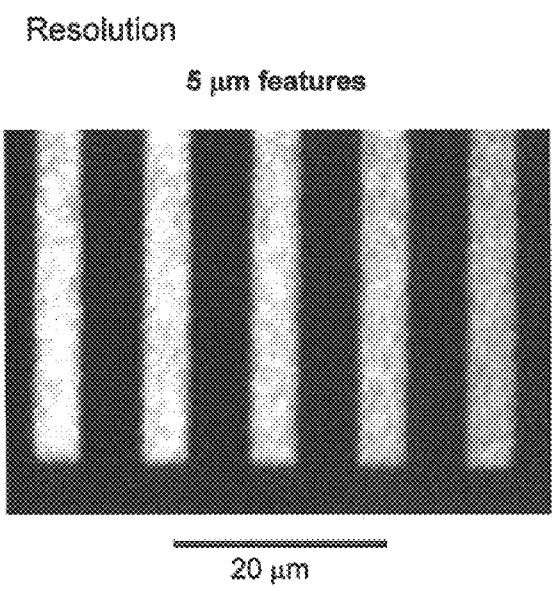 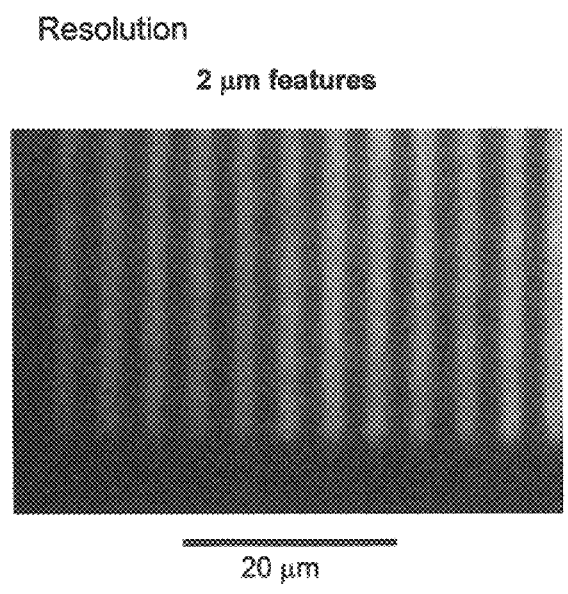
FIG. 2A
FIG. 2B

CHEMICAL AMPLIFICATION FOR THE SYNTHESIS OF PATTERNED ARRAYS

STATEMENT OF RELATED APPLICATIONS

This application claims priority to United States Provisional Application Serial No. 60/030,826 filed Nov. 14, 1996, hereby incorporated by reference in its entirety.

BACKGROUND OF THE INVENTION

Embodiments of the present invention relate to spatially defined chemical synthesis involving lithographic processes. In particular, embodiments of the present invention are directed to novel methods and compositions for synthesizing arrays of diverse polymer sequences, such as polypeptides and polynucleotides. According to a specific aspect of the invention, a method of synthesizing diverse polymer sequences, such as peptides or polynucleotides, is provided. The diverse polymer sequences are useful, for example, in nucleic acid analysis, gene expression monitoring, receptor and nucleic acid binding studies, surface based DNA computation, and integrated electronic circuits and other miniature device fabrication.

Methods of synthesizing polymer sequences such as nucleotide and peptide sequences are known. Methods of synthesizing oligonucleotides are found in, for example, Oligonucleotide Synthesis: A Practical Approach, Gait, ed., IRL Press, Oxford (1984), incorporated herein by reference in its entirety for all purposes. The so-called "Merrifield" solid phase peptide synthesis has been in common use for several years and is discussed in Merrifield, *J. Am. Chem. Soc.* (1963) 85:2149–2154, incorporated herein by reference for all purposes. Solid-phase synthesis techniques have been provided for the synthesis of several peptide sequences on, for example, a number of "pins." See e.g., Geysen et al., *J. Immun. Meth.* (1987) 102:259–274, incorporated herein by reference for all purposes. Other solid-phase techniques involve, for example, synthesis of various peptide sequences on different cellulose disks supported in a column. See Frank and Doring, *Tetrahedron* (1988) 44:6031–6040, incorporated herein by reference for all purposes. Still other solid-phase techniques are discussed in U.S. Pat. No. 4,728,502 (issued to Hamill) and PCT Publication No. WO 90/00626 (Beattie, inventor).

Each of the above techniques produces only a relatively low density array of polymers. For example, the technique discussed in Geysen et al. is limited to producing 96 different polymers on pins spaced in the dimensions of a standard microliter plate.

SUMMARY OF THE INVENTION

Improved methods of forming high density arrays of peptides, polynucleotides, and other polymer sequences in a short period of time have been devised using combinatorial solid phase synthesis. Very Large Scale Immobilized Polymer Synthesis (VLSIPS) technology has greatly advanced combinatorial solid phase polymer synthesis and paved the way to clinical application of deoxyribonucleic acid (DNA) array chips such as those sold under the trademark GENE-CHIP. See Kozal et al., *Nature Medicine,* Vol. 2, pp. 753–759 (1996), incorporated herein by reference in its entirety for all purposes. VLSIPS technology is disclosed in Pirrung et al., U.S. Pat. No. 5,143,854 (see also PCT Publication No. WO 90/15070), Fodor et al., PCT Publication No. WO 92/10092, and PCT Publication No. WO 95/11995; Fodor et al., *Science* (1991) 251:767–777, all incorporated herein by reference in their entirety for all purposes. Known embodiments of VLSIPS technology employ radiation-labile protecting groups and photolithographic masks to achieve spatially defined combinatorial polymer synthesis on a substrate surface. In those embodiments, masks are used to control the selective exposure to radiation in specific locations of a surface provided with linker molecules containing radiation-labile protecting groups. In the exposed locations, the radiation-labile protecting groups are removed. The surface is then contacted with a solution containing a desired monomer. The monomer has at least one site that is reactive with the newly exposed reactive moiety on the linker and at least a second reactive site protected by one or more radiation-labile protecting groups. The desired monomer is then coupled to the unprotected linker molecules. The process can be repeated to synthesize a large number of polymer sequences in specific locations.

Other methods for synthesizing high density polymer arrays employ blocks containing channels for reagent delivery at preselected sites on the substrate. See PCT Publication No. WO 93/09668, incorporated herein by reference for all purposes. In certain embodiments, a block is contacted with the substrate and the reagents necessary to form a portion of the immobilized polymer are permitted to access the substrate via the channel(s). The block or substrate can be rotated and the process repeated to form arrays of polymers on the substrate. The block channel method can be combined with light-directed methodologies.

Certain embodiments of the present invention provide novel methods, compositions, and devices useful in synthesizing novel high density arrays of diverse polymer sequences. The polymer sequences are fashioned from individual synthesis intermediates and include diverse naturally or non-naturally occurring peptides, nucleotides, polpeptides or polynucleotides. The methods of the present invention utilize a novel chemical amplification process using a catalyst system which is initiated by radiation to assist in the synthesis the polymer sequences. Methods of the present invention include the use of photosensitive compounds which act as catalysts to chemically alter the synthesis intermediates in a manner to promote formation of polymer sequences. Such photosensitive compounds include what are generally referred to as radiation-activated catalysts (RACs), and more specifically photo activated catalysts (PACs). The RACs can by themselves chemically alter the synthesis intermediate or they can activate an autocatalytic compound which chemically alters the synthesis intermediate in a manner to allow the synthesis intermediate to chemically combine with a later added synthesis intermediate or other compound.

According to one embodiment of the present invention, one or more linker molecules are bound to or otherwise provided on the surface of a substrate, such as a glass plate. The unbound portion of the linker molecule, also referred to as the terminal or free end of the linker molecule, has a reactive functional group which is blocked, protected or otherwise made unavailable for reaction by a removable protective group. Once the protective group is removed, the functional group is made available for reaction, i.e. the reactive functional group is unblocked. A photo activated catalyst (PAC) is also located or otherwise provided on the surface of the substrate in the vacinity of the linker molecules. An autocatalytic compound may also be present on the surface of the substrate. The photo activated catalyst by itself or in combination with additional catalytic components is referred to herein as a catalyst system.

Using lithographic methods and techniques well known to those of skill in the art, a set of first selected regions on the surface of the substrate is exposed to radiation of certain wavelengths. The radiation activates the PAC which then either directly or through an autocatalytic compound catalytically removes the protecting group from the linker molecule making it available for reaction with a subsequently added synthesis intermediate.

According to one embodiment of the present invention, the radiation causes the structure of the PAC to change and to produce a catalyst capable of initiating the autocatalytic compound, also referred to herein as an enhancer, to undergo a reaction producing at least one product that removes the protective groups from the linker molecules in the first selected regions. The use of PACs and autocatalytic compounds advantageously amplifies through catalysis the number of linker molecules having their protective groups removed. Stated differently, the radiation initiates a chemical reaction which catalyzes the removal of a large number of protective groups. With the protective groups removed, the reactive functional groups of the linker molecules are made available for reaction with a subsequently added synthesis intermediate or other compound.

The substrate is then washed or otherwise contacted with an additional synthesis intermediate that reacts with the exposed functional groups on the linker molecules to form a sequence. In some preferred embodiments, the enhancers are autocatalytic compounds or groups that undergo autocatalysis when initiated by a RAC such as a PAC. The synthesis intermediate also has a reactive functional group which is blocked or otherwise made unavailable for reaction by a removable protective group. In this manner, a sequence of monomers of any desired length can be created by stepwise irradiating the surface of the substrate to initiate a catalytic reaction to remove a protective group from a reactive functional group on a already present synthesis intermediate and then introducing a monomer, i.e. a synthesis intermediate, that will react with the reactive functional group, and that will have a protective group for later removal by a subsequent irradiation of the substrate surface.

Accordingly, a second set of selected regions on the substrate which may be the same or different from the first set of selected regions on the substrate is, thereafter, exposed to radiation and the removable protective groups on the synthesis intermediates or linker molecules are removed. The substrate is then contacted with an additional subsequently added synthesis intermediate for reaction with exposed functional groups. This process is repeated to selectively apply synthesis intermediates until polymers of a desired length and desired chemical sequence are obtained. Protective groups on the last added synthesis intermediate in the polymer sequence are then optionally removed and the sequence is, thereafter, optionally capped. Side chain protective groups, if present in the polymer sequence, are also removed. The technique, when it employs photon radiation, is referred to as "photochemical amplification for the synthesis of patterned arrays" or "PASPA".

According to one embodiment of the present invention, the RAC produces an acid when exposed to radiation; the enhancer is an ester labile to acid catalyzed thermolytic cleavage which itself produces an acid; the protecting group is an acid removable protecting group, and the monomer is a nucleotide containing an acid removable protecting group at its C-5' hydroxyl group, for example when synthesis is carried out in the 3' to 5' direction. It is to be understood that the teachings of the present invention are equally useful in carrying out synthesis of polynucleotides in the 5' to 3' direction. In that instance, the protective group is present at the 3' hydroxyl group. In an alternate embodiment of the present invention, the monomer is an amino acid containing an acid removable protecting group at its amino or carboxy terminus and the linker molecule terminates in an amino or carboxy acid group bearing an acid removable protective group.

Using the techniques disclosed herein, it is possible to advantageously irradiate relatively small and precisely known locations on the surface of the substrate. The radiation does not directly cause the removal of the protective groups, such as through a photochemical reaction upon absorption of the radiation by the synthesis intermediate or linker molecule itself, but rather the radiation acts as a signal to initiate a chemical catalytic reaction which removes the protective group in an amplified manner. Therefore, the radiation intensity as used in the practice of the present invention to initiate the catalytic removal by a catalyst system of protecting groups can be much lower than, for example, direct photo removal, which can result in better resolution when compared to many non-amplified techniques.

The present invention is advantageous because it makes possible the synthesis of polymers of any desired chemical sequence at known locations on a substrate with high synthesis fidelity, small synthesis feature, and improved manufacturability. Embodiments of the present invention are useful in fabricating high density nucleic acid probe arrays or immobilizing nucleic acid sequences on a surface of a substrate. High density nucleic acid probe arrays provide an efficient means to analyze nucleic acids, to monitor gene expression and to perform computation.

It is therefore an object of the present invention to provide methods of manufacturing high density polymer arrays using chemical amplification techniques. It is a further object of the present invention to provide methods of manufacturing polymer arrays using less time and lower radiation intensities to improve polymer purity, to improve the spatial resolution and contrast between polymer and substrate and to decrease the area on the substrate where polymer sequences can be synthesized allowing many and different polymer sequences on the same substrate. It is a still further object of the present invention to provide methods of removing protecting groups from synthesis intermediates in the formation of polymer sequences using photosensitive compounds to initiate catalytic reactions. It is an even still further object of the present invention to improve precision, contrast, and ease of manufacture in the production of polymer arrays.

These and other objects, features and advantages of the present invention will become apparent by reference to the remaining portions of the specification and the attached drawings.

BRIEF DESCRIPTION OF THE DRAWINGS

In the course of the detailed description of certain preferred embodiments to follow, reference will be made to the attached drawings, in which.

FIG. 2 is an image showing 5 $\mu$m and 2 $\mu$m features obtained by the process of the present invention.

DETAILED DESCRIPTION OF CERTAIN PREFERRED EMBODIMENTS

Figure 1:
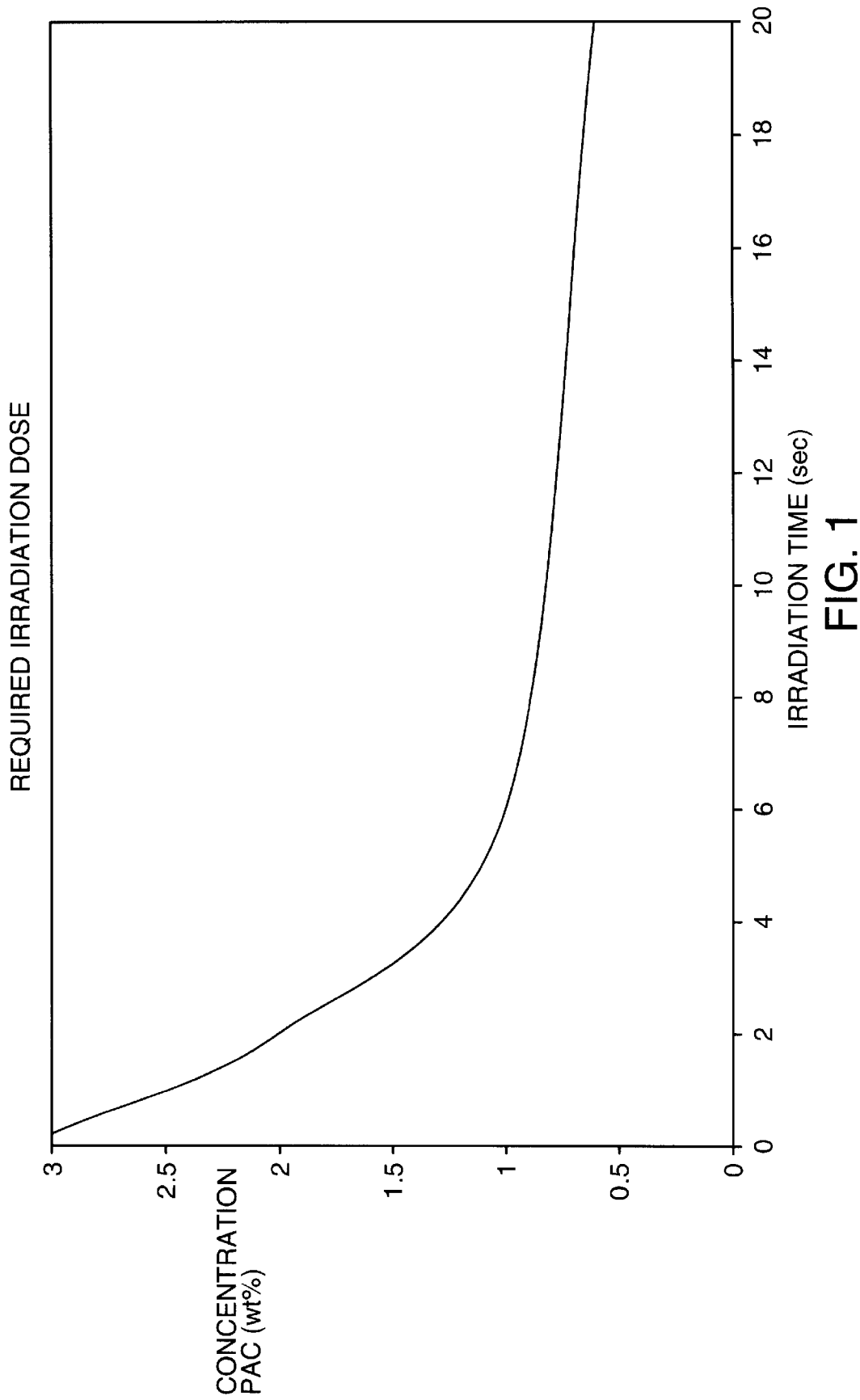
FIG. 1 is a graph of concentration of PAC versus irradiation time in seconds.

The principles of the present invention may be applied with particular advantage to provide a method of preparing selected polymer sequences in a precise manner in a polymer array by using radiation to initiate the catalytic removal of protective groups to allow polymer chain formation in a stepwise method.

As used herein, the following terms are intended to have the following general meanings:

1. Ligand: A ligand is a molecule that is recognized by a receptor. Examples of ligand that can be investigated by this invention include, but are not restricted to, agonists and antagonists for cell membrane receptors, toxins and venoms, viral epitopes, hormones, opiates, steroids, peptides, enzyme substrates, cofactors, drugs, lectins, sugars, oligonucleotides, nucleic acids, oligosaccharides, and proteins.

2. Monomer: A monomer is a member of the set of small molecules which are or can be joined together to form a polymer or a compound composed of two or more members. The set of monomers includes but is not restricted to, for example, the set of common L-amino acids, the set of D-amino acids, the set of synthetic and/or natural amino acids, the set of nucleotides, and the set of pentoses and hexoses, each set of which is readily known to those of skill in the art. The particular ordering of monomers within a polymer is referred to herein as the "sequence" of the polymer. As used herein, "monomers" refers to any member of a basis set for synthesis of a polymer, and is not limited to a single "mer". For example, dimers of the 20 naturally occurring L-amino acids form a basis set of 400 monomers for synthesis of polypeptides. Monomers can also include trimers, oligomers, polymers and so forth. Different basis sets of monomers may be used at successive steps in the synthesis of a polymer. Furthermore, each of the sets may include protected members which are modified after synthesis. The invention is described herein primarily with regard to the preparation of molecules containing sequences of monomers such as amino acids, but could readily be applied in the preparation of other polymers. Such polymers include, for example, both linear and cyclic polymers of nucleic acids, polysaccharides, phospholipids, and peptides having either α-, β-, or ω-amino acids, heteropolymers in which a known drug is covalently bound to any of the above, polynucleotides, polyurethanes, polyesters, polycarbonates, polyureas, polyamides, polyethyleneimines, polyarylene sulfides, polysiloxanes, polyimides, polyacetates, or other polymers which will be apparent upon review of this disclosure. Such polymers are "diverse" when polymers having different monomer sequences are formed at different predefined regions of a substrate. Methods of cyclization and polymer reversal of polymers are disclosed in copending application Ser. No. 796,727, filed Nov. 22, 1991, entitled "POLYMER REVERSAL ON SOLID SURFACES," incorporated herein by reference for all purposes.

3. Peptide: A peptide is a polymer in which the monomers are α-amino acids and are joined together through amide bonds, alternatively referred to as a polypeptide. Amino acids may be the L-optical isomer or the D-optical isomer. The term "polypeptide" as used herein refers to two or more amino acid monomers in length or greater and often includes more than 20 amino acid monomers or monomers on the order of hundreds. Standard abbreviations for amino acids are used (e.g., P for proline). Identification of amino acids and their abbreviations are well-known and are included in Stryer, Biochemistry, Third Ed., 1988, which is incorporated herein by reference for all purposes.

4. Receptor: A receptor is a molecule that has an affinity for a ligand. Receptors may be naturally-occurring or man-made molecules. They can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants, viruses, cells, drugs, polynucleotides, nucleic acids, peptides, cofactors, lectins, sugars, polysaccharides, cellular membranes, and organelles. Receptors are sometimes referred to in the art as antiligands. As the term receptors is used herein, no difference in meaning is intended. A "Ligand Receptor Pair" is formed when two molecules have combined through molecular recognition to form a complex. Specific examples of receptors which can be investigated by this invention include but are not restricted to:

a.) Microorganism receptors: The determination of ligands that bind to microorganism receptors such as specific transport proteins or enzymes essential to survival of microorganisms would be a useful tool for discovering new classes of antibiotics. Of particular value would be antibiotics against opportunistic fungi, protozoa, and bacteria resistant to antibiotics in current use.

b.) Enzymes: For instance, a receptor can comprise a binding site of an enzyme such as an enzyme responsible for cleaving a neurotransmitter; determination of ligands for this type of receptor to modulate the action of an enzyme that cleaves a neurotransmitter is useful in developing drugs that can be used in the treatment of disorders of neurotransmission.

c.) Antibodies: For instance, the invention may be useful in investigating a receptor that comprises a ligand-binding site on an antibody molecule which combines with an epitope of an antigen of interest; analyzing a sequence that mimics an antigenic epitope may lead to the development of vaccines in which the immunogen is based on one or more of such sequences or lead to the development of related diagnostic agents or compounds useful in therapeutic treatments such as for autoimmune diseases (e.g., by blocking the binding of the "self" antibodies).

d.) Nucleic Acids: Sequences of nucleic acids may be synthesized to establish sequences recognized by various receptor molecules, such as protein or other DNA or RNA molecules. Nucleic acids within the scope of the present invention include naturally occurring or synthetic nucleic acids, nucleic acid analogs, modified nucleic acids, nucleic acids containing modified nucleotides, modified nucleic acid analogs, peptide nucleic acids and the like or mixtures thereof.

e.) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides and others are discussed in, for example, PCT Publication No. WO 90/05746, WO 90/05749, and WO 90/05785, which are incorporated herein by reference for all purposes.

f.) Hormone receptors: Determination of the ligand which binds with high affinity to a receptor such as the receptors for insulin and growth hormone is useful in the development of, for example, an oral replacement of the daily injections which diabetics must take to relieve the symptoms of diabetes or a replacement for growth hormone. Other examples of hormone receptors include the vaso-constrictive hormone receptors; determination of ligands for these receptors may lead to the development of drugs to control blood pressure.

g.) Opiate receptors: Determination of ligands which bind to the opiate receptors in the brain is useful in the development of less-addictive replacements for morphine and related drugs.

5. Substrate: A material having a rigid or semi-rigid surface usually made from glass or suitable polymer materials. In many embodiments, at least one surface of the substrate will be substantially flat, although in some embodiments it may be desirable to physically separate synthesis regions for different polymers with, for example, wells, raised regions, etched trenches, or the like. In some embodiments, the substrate itself contains wells, trenches, flow through regions, etc. which form all or part of the synthesis regions. According to other-embodiments, small beads may be provided on the surface, and compounds synthesized thereon optionally may be released upon completion of the synthesis. Substrates are well known in the art and are readily commercially available through vendors such as USPG, PPG Industries, AFG Industries and others.

6. Protective Group: A material which may be selectively removed to expose an active site such as, in the specific example of an amino acid, an amine group. By way of illustration, protecting groups include but are not limited to those that are photolabile (see Fodor et al., PCT Publication No. WO 92/10092 (previously incorporated by reference), U.S. Ser. No. 07/971,181, filed Nov. 2, 1992, and U.S. Ser. No. 08/310,817, filed Sep. 22, 1994 (all of which are incorporated herein by reference in their entirety for all purposes)), acid labile, and base labile. For an extensive listing of protective groups useful in the practice of the present invention, see also Greene, T. W. and Wuts, P. G. M., Protective Groups in Organic Synthesis, (1991), incorporated herein by reference in its entirety for all purposes. Useful representative acid sensitive protective groups include dimethoxytrityl (DMT), tert-butylcarbamate (tBoc) and trifluoroacetyl (Tfa). Useful representative base sensitive protective groups include 9-fluorenylmethoxycarbonyl (Fmoc), isobutyrl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyl, tert-butyloxycarbonyl, 1-carbobenzoxamido-2,2,2-trifluoroethyl, 2,6-dichlorobenzyl, 2-(3,5-dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester and the like.

7. Predefined Region: A predefined region is a localized area on a substrate which is, was, or is intended to be used for formation of a selected polymer and is otherwise referred to herein in the alternative as "reaction" region, a "selected" region, or simply a "region." The predefined region may have any convenient shape, e.g., circular, rectangular, elliptical, wedge-shaped, etc. In some embodiments, a predefined region and, therefore, the area upon which each distinct polymer sequence is synthesized is smaller than about 1 mm$^2$, more preferably less than 1 cm$^2$, and still more preferably less than 0.5 mm2. In most preferred embodiments, the regions have an area less than about 10,000 $\mu m^2$ or, more preferably, less than 100 $\mu^2$m. Within these regions, the polymer synthesized therein is preferably synthesized in a substantially pure form.

8. Substantially Pure: A polymer is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor. Preferably the region is sufficiently pure such that the predominant species in the predefined region is the desired sequence. According to preferred aspects of the invention, the polymer is at least 5% pure, more preferably more than 10% to 20% pure, more preferably more than 95% pure, where purity for this purpose refers to the ratio of the number of polymer molecules formed in a predefined region having a desired sequence to the total number of molecules formed in the predefined region.

9. Catalyst: A catalyst is any material that is not consumed in a chemical reaction and that affects the rate of the reaction. Reactions that are affected by catalysts are termed catalytic reactions. Autocatalytic reactions are reactions in which at least one of the products is also a catalyst for the reaction. An autocatalyst is a material that undergoes a reaction that produces a product that is also a catalyst for that same reaction. Some autocatalytic reactions have a relatively slow rate of reaction at the initial stage but the reaction is accelerated as it proceeds as more catalytic product is accumulated. Where a substance or a combination of substances undergoes two or more simultaneous reactions that yield different products, the distribution of products could be influenced by the use of a catalyst that selectively accelerates one reaction relative to the other(s).

10. Radiation-Activated Catalyst (RAC): A radiation activated catalyst (RAC) is a compound or group which produces at least one catalyst when exposed to radiation. RACs include but are not limited to radicals, acids, bases, ions, and metals.

11. Enhancer: An enhancer is any material that amplifies a radiation-initiated chemical signal so as to increase the effective quantum yield of the radiation. Enhancers include but are not limited to catalytic materials. The use of an enhancer in radiation-assisted chemical processes is termed chemical amplification. Chemical amplification has many benefits. Non limiting examples of the benefits of chemical amplification include the ability to decrease the time and intensity of irradiation required to cause a desired chemical reaction. Chemical amplification also improves the spatial resolution and contrast in patterned arrays formed using this technique.

12. Radiation sensitizer: A radiation sensitizer is any material that shifts the wavelengths of radiation required to initiate a desired reaction.

The present invention provides methods, devices, and compositions for the formation of arrays of large numbers of different polymer sequences. The methods and compositions provided herein involve the conversion of radiation signals into chemical products in an amplified manner that are particularly useful in polymer synthesis. The invention also includes the arrays formed using the methods and compositions disclosed herein. One aspect of the invention includes methods, compositions, and devices for the synthesis of an array of different polymers in selected and predefined regions of a substrate. Another aspect of the invention includes those arrays and various methods of using them.

Such arrays are used in, for example, nucleic acid analysis. Polynucleoiide or nucleic acid arrays are especially suitable for checking the accuracy of previously elucidated sequences and for detecting mutations and polymorphisms. Such arrays are also used in screening studies to evaluate their interaction with receptors such as antibodies and nucleic acids. For example, certain embodiments of the invention provide for the screening of peptides to determine which if any of a diverse set of peptides has strong binding affinity with a receptor.

In some embodiments, the arrays formed by the present invention are used in competitive assays or other well-known techniques to screen for compounds having certain activities. For example, vast collections of synthetic or natural compounds are immobilized on predefined regions of a substrate. The reaction of the immobilized compounds (or compound) with various test compositions such as the members of a chemical library or a biological extract are tested by dispensing small aliquots of each member of the library or extract to a different region. In one embodiment, a large collection of human receptors is deposited on a substrate, one in each region to form an array. A plant or animal extract is then screened for binding to various receptors of the array.

Nucleic acid sequences can also be immobilized in specific locations or predefined regions of a substrate using the current invention. In some embodiments, such immobilized nucleic acid arrays are used in hybridization assays for gene expression monitoring, nucleic acid amplifications, nucleic acid computation, and nucleic acid analysis in general.

The present invention has certain features in common with the radiation directed methods discussed in U.S. Pat. No. 5,143,854, previously incorporated herein by reference. The radiation-directed methods discussed in that patent involve activating predefined regions of the substrate and then contacting the substrate with a preselected monomer solution. The predefined regions can be activated with, for example, a light source shown through a mask (much in the manner of photolithographic techniques used in integrated circuit fabrication). Other regions of the substrate remain inactive because they are blocked by the mask from illumination. Thus, a light pattern defines which regions of the substrate react with a given monomer. By repeatedly activating different sets of predefined regions and providing different monomer compositions thereto, a diverse array of polymers is produced on or near the substrate.

In some preferred embodiments of the present invention, a substrate with a linker having a protective group is provided with a radiation-activated catalyst and an enhancer. The RAC is selectively irradiated to generate a catalyst in preselected regions. The catalyst and the enhancer assist the removal of the protective groups on the linker. The linker, having a newly exposed reactive group, is contacted with a monomer capable of reacting with the linker. The monomer also has a protective group which can be removed in a subsequent reaction step. In this step wise manner, diverse arrays of polymers are synthesized at preselected regions of a substrate.

Photochemical Amplification for the Synthesis of Patterned Arrays

One embodiment of the present invention includes a photochemical amplification method wherein photon radiation signals are converted into chemical signals in a manner that increases the effective quantum yield of the photon in the desired reaction. The use of photochemical amplification in methods of synthesizing patterned arrays (PASPA) is particularly advantageous since the time and the intensity of irradiation required to remove protective groups is decreased relative to known photochemical methods. The methods of the present invention advantageously produce patterned arrays having improved spatial resolution and contrast.

In general, radiation signals are detected by a catalyst system including, for example, a photo activated catalyst (PAC). The catalyst activates an enhancer, which increases the effective quantum yield of the photons in subsequent chemical reactions. Such subsequent reactions include the removal of protective groups in the synthesis of patterned arrays.

In certain embodiments, a photo activated acid catalyst (PAAC) is irradiated. The resulting acid produced from the PAAC activates an enhancer to undergo an acid-catalyzed reaction to itself produce an acid that removes acid labile protecting groups from a linker molecule or synthesis intermediate. The combination of PACs and enhancers converts and amplifies the photon signal irradiated on the surface of the substrate. Because of the amplification, the effective quantum yield of the radiation directed at the surface of the substrate is much larger than one, resulting in high sensitivity.

According to one embodiment of the present invention, linker molecules having reactive functional groups protected by protecting groups are provided on the surface of a substrate. A catalyst system including a PAC and an enhancer are also provided on the surface. A set of selected regions on the surface of the substrate is exposed to radiation using well-known lithographic methods discussed, for example, in Thompson, L. F.; Wllson, C. G.; and Bowden, M. J., Introduction to Microlithography; *American Chemical Society*, 1994, pp. 212–232, incorporated herein by reference in its entirety for all purposes.

The PAC catalyst activated by the region-selective irradiation discussed above acts to initiate a reaction of the enhancer. The enhancer produces at least one product that removes the protecting groups from the linker molecules in the first selected regions. Preferably, the enhancer is capable of removing protective groups in a catalytic manner. The substrate is then washed or otherwise contacted with a first monomer that reacts with exposed functional groups on the linker molecules. Those bound monomers are termed first-bound monomers.

A second set of selected regions is, thereafter, exposed to radiation. The radiation-initiated reactions remove the protecting groups on molecules in the second set of selected regions, i.e. the linker molecules and the first-bound monomers. The substrate is then contacted with a second monomer containing a removable protective group for reaction with exposed functional groups. This process is repeated to selectively apply monomers until polymers of a desired length and desired chemical sequence are obtained. Protective groups are then optionally removed and the sequence is, thereafter, optionally capped. Side chain protective groups, if present, are also optionally removed.

In one preferred embodiment, the monomer is a 2'-deoxynucleoside phosphoramidite containing an acid removable protecting group at its 5' hydroxyl group. As stated previously, in an alternate embodiment, the protecting group is present at the 3' hydroxyl group if synthesis of the polynucleotide is from the 5' to 3' direction. The nucleoside phosphoroamidite is represented by the following formula:

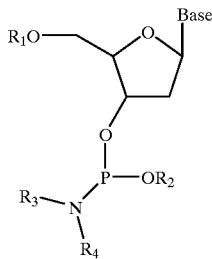

wherein the base is adenine, guanine, thymine, or cytosine, $R_1$ is a protecting group which makes the 5' hydroxyl group unavailable for reaction and includes dimethoxytrityl, tert-butyloxycarbonyl or any of the protecting groups previously identified; $R_2$ is cyanoethyl, methyl, t-butyl, trimethylsilyl and the like and $R_3$ and $R_4$ are isopropyl, cyclohexone and the like. Exocyclic amines present on the bases can also be protected with acyl protecting groups such as benzoyl, isobutyryl, phenoxyacetyl and the like. The linker molecule contains an acid- or base -removable protecting group. Useful linker molecules are well known to those skilled in the art and representative examples include oligo ethers such as hexaethylene glycol, oligomers of nucleotides, esters, carbonates, amides and the like. Useful protecting groups include those previously listed and others known to those skilled in the art In another preferred embodiment, the monomer is an amino acid containing an acid- or base- removable protecting group at its amino or carboxy terminus and the linker molecule terminates in an amino or carboxy acid group bearing an acid- or base removable protecting group. Protecting groups include tert-butyloxycarbonyl, 9-fluorophenylmethoxycarbonyl and any of the protective groups previously mentioned and others known to those skilled in the art.

It is apparent to those skilled in the art that photochemically amplified radiation-based activation is not limited to photo activated enhancers or catalysts or to acid or base production cascades. Various compounds or groups can produce catalysts or enhancers in response to radiation exposure. Non-limiting examples include photogeneration of radicals using diphenylsulfide, benzoylperoxide, 2,2'-azobis(butyronitrile), benzoin and the like; cations such as triarylsulfonium salts, diaryl iodonium salts and the like; and anions.

Radiation-Activated Catalysts (RACs)

Useful RACs within the scope of the present invention include those that are capable of directly or indirectly catalyzing the removal of a protective group from a linker moleculer or polymer chain and are chosen based upon their sensitivity to radiation at certain wavelengths. Useful wavelengths include those within the infrared, visible, ultraviolet and X-ray ranges. In one embodiment, the RACs produce acids or bases upon exposure to radiation of certain wavelengths for use in activating enhancers or other catalysts in the chemically amplified removal of protecting groups.

Preferably, the RAC chosen for a particular synthesis strategy does not unduly interfere with subsequent or previous synthesis steps in the formation of the polymer. Surprisingly, the method of the present invention advantageously allows the use of photocatalysts or products of photocatalysts that can be detrimental in known methods of synthesizing polymer arrays. For example, some PAACs produce strong acids that cause significant depurination and thus could not be used directly for polynucleotide synthesis. However, the method of the present invention allows the use of these types of PAACs that produce strong acids since only small amounts of the PAACs are needed and accordingly only a small amount of strong acid is produced. Another important consideration is the radiation sensitivity of the various compounds employed.

One preferred class of RACs include PAACs such as naphthoquinone diazide sulfonic acids such as those disclosed by Kosar, Light Sensitive Systems, John Wiley & Sons, 1965, pp. 343 to 352, incorporated herein by reference in its entirety for all purposes. These PAACs form an acid in response to radiation of different wavelengths ranging from visible to X-ray. Preferred PAACs include the 2, 1, 4 diazonaphthoquinone sulfonic acid esters and the 2, 1, 5-diazonaphthoquinone sulfonic acid esters. Other useful PACs include the family of nitrobenzyl esters, and the s-triazine derivatives. Suitable s-triazine acid generators are disclosed, for example, in U.S. Pat. No. 4,189,323, incorporated herein by reference. Non-ionic PAACs including halogenated non-ionic, photoacid generating compounds such as, for example, 1,1-bis[p-chorophenyl]-2,2,2-trichloroethane (DDT); 1,1- bis[p-methoxyphenyl]-2,2,2-trichloroethane; 1,2,5,6,9,10-hexabromocyclododecane; 1,10-dibromodecane; 1,1-bis[p-chlorophenyl]-2,2-dichloroethane; 4,4dichloro-2-(trichloromethyl) benzhydrol (Kelthane); hexachlorodimethyl sulfone; 2-chloro-6-(trichloromethyl) pyridine; o,o-diethyl-o-(3,5,6-trichloro-2-pyridyl) phosphorothionate; 1,2,3,4,5,6 hexachlorocyclohexane; N(1,1-bis[p-chlorophenyl]-2,2,2 trichloroethyl) acetamide; tris [2,3-dibromopropyl]isocyanurate; 2,2-bis [p-chlorophenyl]-1,1 dichloroethylene; tris [trichloromethyl] striazine; and their isomers, analogs, homologs, and residual compounds are also suitable for some applications. Suitable PAACs are also disclosed in European Patent Application Nos. 0164248 and 0232972, both incorporated by reference for all purposes. PAACs that are particularly preferred for deep UV exposure include 1,1-bis (p-chlorophenyl)-2,2,2-trichloroethane (DDT); 1,1-bis (p-methoxyphenol)-2,2,2,-trichloroethane; 1,1-bis (chlorophenyl)-2,2,2 trichloroethanol; tris (1,2,3-methanesulfonyl) benzene; and tris (trichloromethyl) triazine.

Onium salts are preferred for some embodiments as PACs. When synthesizing polynucleotide arrays, a radiation sensitizer is employed to shift the radiation sensitivity of the onium salts away from wavelengths damaging to the starting materials. Suitable radiation sensitizers for use with onium salts or other RACs are well known in the art and include benzophenone, thiophene, fluorene, anthraquinone, quinoline, phenanthracene, flavone, micheler's ketone, chrysene, anthracene, eosin and the like. It is to be understood that additional sensitizers are well known to those skilled in the art and are readily identifiable based upon the present disclosure.

Examples of onium salts useful in the present invention include those having halogen (i.e. I, Br, Cl etc.) complex anions of divalent to heptavalent metals or non-metals, for example, Sb, Sn, Fe, Bi, Al, Ga, In, Ti, Zr, Sc, Cl, Cr, Hf, and Cu as well as B, P, and As. Examples of suitable onium salts are diaryl-diazonium salts and onium salts of group VI and VII of the Periodic Table, for example, halonium salts, quaternary ammonium, phosphonium and arsonium salts, aromatic sulfonium salts and sulfoxonium salts or seleonium salts. Examples of suitable preferred onium salts can be found in U.S. Pat. Nos. 4,442,197; 4,603,101; and 4,624,912, all incorporated herein by reference. Sulfonium analogs can be prepared using Group VI elements such as O, S, Se, Te. Onium analogs can be prepared by using Group VII elements such as I, Br, and Cl. For a review on onium salts as photoacid generators, see Pappas, *J Imaging Technology* (1985), 11,146, incorporated herein by reference. Another group of suitable acid generators is the family of sulfonated esters including sulfonyloxy ketones. Suitable sulfonated esters have been reported in *J. of Photopolymer Science and Technology* (1991), 4, 3, 337–340, incorporated herein by reference, including benzoin tosylate, t-butylphenyl alpha-(p-toluenesulfonyloxy)-acetate, and t-butyl alpha-(p-toluenesulfonyloxy)-acetate. Both ionic, including di-tert-butylphenyl iodonium triflate (TBI-T), di-tertbutylphenliodonium caimphorsulfonate (TBI-CAM) and di-tert-butylphenyl iodonium dichloracetate (TBI-DCA), and nonionic, including napthalimidotriftete and phthalimidotosylate or mixture of those photoacids are useful in the present invention. Useful PACs within the scope of the present invention include

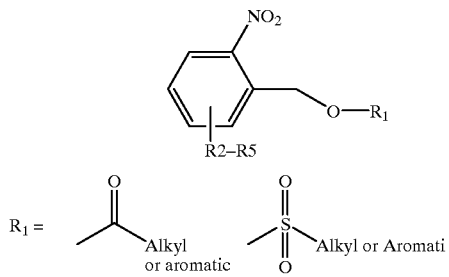

$R_2$–$R_5$ = alkyl, CN, NO2, O-alkyl, H, OH, NH2, N(alkyl)2

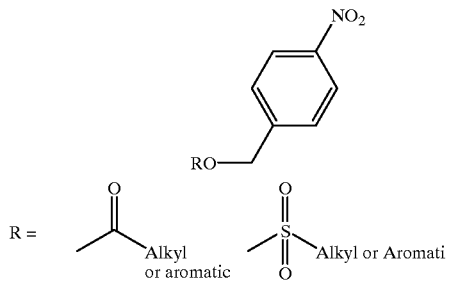

Alkyl refers to saturated or unsaturated, straight chain or branched, carbon atoms having from 1 to 50 carbons, preferably from 1 to 30 carbon atoms and more preferably from 1 to 10 carbon atoms. Aromatic groups include straight chain or cyclic aromatics, substituted or unsubstituted having from 1 to 50 carbons, preferably from 1 to 30 carbon atoms and more preferably from 1 to 10 carbon atoms. One preferred PAC for polynucleotide synthesis is the o-nitrobenzyl ester of toluenesulfonic acid, such as the 2-nitro-3,4-dimethoxbenzyl tosylate having the structure:

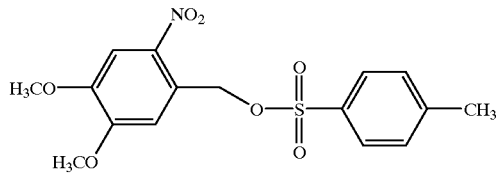

When irradiated, the ester produces catalytic amounts of p-toluenesulfonic acid. Other PACs useful in the practice of the present invention include the following:

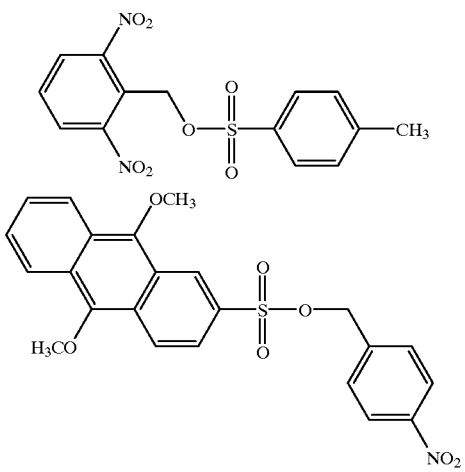

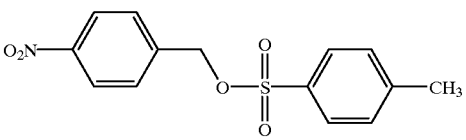

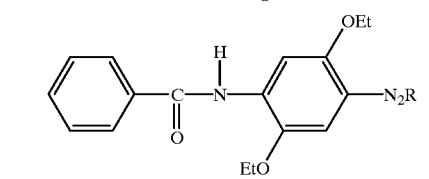

wherein R is sulfonate, tosylate, mesolate, $PF_6^-$ or $BF_4^-$ with or without the presence of a sensitizer of the formula:

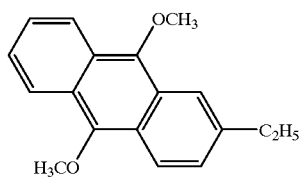

Catalytic Enhancers

In some preferred embodiments of polynucleotide synthesis, masked acids including esters, anhydrides, and nitrites are used as autocatalysts. In one preferred specific embodiment, the RAC is a PAAC which generates an acid upon exposure to radiation of suitable wavelength. The catalytic enhancer is an ester labile to acid-catalyzed thermolytic cleavage by the acid produced by the PAAC. The enhancer, itself, produces an acid which is used to removed an acid labile protective group. Post-exposure baking of the substrate is required, in some embodiments, because the acid autocatalysis occurs only when heated. A preferred catalytic masked acid for polynucleotide synthesis is the ester of the pentafluorobenzoic acid such as the 1,4-cyclohex-2-enediylbis(pentafluorobenzoate) illustrated below:

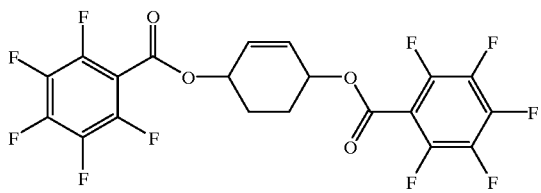

The acid catalyzes the cleavage of the ester to produce pentafluorobenzoic acid, benzene, and regenerates the catalytic acid. The acid produced effectively removes acid-labile groups, yet does not cause the degradation or depurination of polynucleotides. Other useful catalytic enhancers within the scope of the present invention include those identified in Ichimura, Mol. Cryst. Liq. Cryst. (1996) vol. 280 pp. 307–312 and Ichimura, Chem. Lett. (1995) pp. 551–552 each of which are hereby incorporated by reference in their entireties and those of the following general formulas where R is any suitable group:

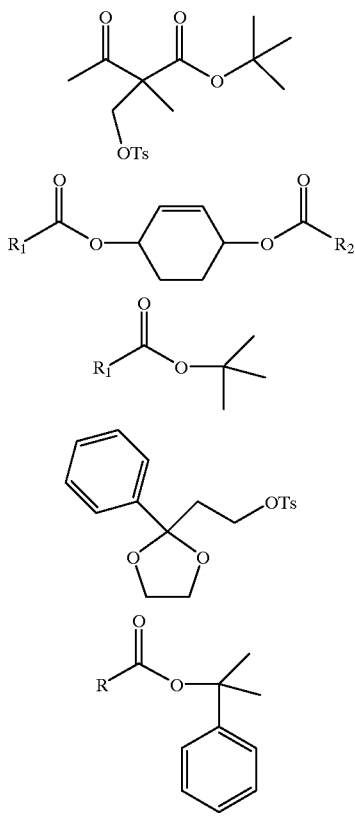

The selection of temperature is also dependent upon the subsequent synthesis steps. A too high temperature may damage synthesis intermediates. A too low temperature may not be sufficient to activate thermolysis. A suitable range of temperatures to induce acid-catalyzed thermolysis of 1,4-cyclohex-2-enediylbis (pentafluorobenzoate) is 70–100° C.

Using the guidance provided herein, suitable reaction conditions (including temperature) can be determined for a variety of embodiments by one having skill in the art. For example, the chemical and thermal stability of various compounds is known or can be determined readily. A series of experiments showing the efficiency of synthesis as a function of temperature, irradiation intensity, or exposure time is within the skill of those in the art.

If an acid autocatalysis system is used, the protecting group could, but not necessarily, be an acid removable protecting group, and the monomer could be a nucleotide containing an acid removable protecting group at its C-5' or C-3' hydroxyl group.

Radiation, Sensitizers and Substrates

The selection of radiation sources is based upon the sensitivity spectrum of the RAC. Potential damage to synthesis substrates, intermediates, or products is also considered. In some preferred embodiments, the radiation could be ultraviolet (UV), infrared (IR), or visible light. In a specific embodiment, the radiation source is a light beam with a wavelength in the range of from 190–500 nm, preferably from 250–450 nm, more preferably from 365–400 nm. Specific radiation wavelengths include 193 nm, 254 nm, 313 nm, 340 nm, 365 nm, 396 nm, 413 nm, 436 nm, and 500 nm. Suitable light sources include high pressure mercury arc lamps and are readily commercially available from Oriel, OAI, Cannon, A,B Manufacturing. The sensitivity spectrum of the RAC can be altered by providing radiation sensitizers. The energy of the sensitizer must be matched to the PAC and include 2-ethyl-9,10-dimethoxy-anthracene, perylene, phenothiazine, xanthone and the like. Many radiation sensitizers are known to those skilled in the art and include those previously mentioned. It is to be understood that one of ordinary skill in the art will be able to readily identify additional radiation sensitizers based upon the present disclosure.

In prefereed embodiments, the substrate is conventional glass, pyrex, quartz, any one of a variety of polymeric materials, or the like. Of course, the substrate may be made from any one of a variety of materials such as silicon, polystyrene, polycarbonate, or the like. In operation, the surface of the substrate is appropriately treated by cleaning with, for example, organic solvents, methylene chloride, DMF, ethyl alcohol, or the like. Optionally, the substrate may be provided with appropriate linker molecules on the surface thereof. The linker molecules may be, for example, aryl acetylene, ethylene glycol oligomers containing from 2–10 monomers or more, diamines, diacids, amino acids, or combinations thereof. Thereafter, the surface is provided with protected surface active groups such as tertbutyloxycarbonyl (TBOC) or fluorenylmethoxycarbonyl (FMOC) protected amino acids. Such techniques are well known to those of skill in the art.

In light-directed methods, the light shown through the mask is diffracted to varying degrees around the edges of the dark regions of the mask. Thus, some undesired removal of photosensitive protecting groups at the edges of "dark" regions occurs. This effect is exacerbated by the repeated mask translations and subsequent exposures, ultimately leading to inhomogeneous synthesis sites at the edges of the predefined regions. Since in one embodiment of the present invention, the RAC catalyzes cleavage of the enhancer to produce an acid used to remove an acid-labile protective group, the effective quantum yield of the radiation is much larger than one, resulting in a high sensitivity. Additionally, the sensitivity of the process can be tuned by controlling the concentrations of the RAC or photocatalyst and the enhancer on the polymer matrix. Higher concentration results in a higher sensitivity. Other advantages will be apparent to those skilled in the art.

Application of Chemical Amplification Techniques

The techniques of the present invention are useful in many fields, particularly in nucleic acid analysis, gene expression monitoring, amplification of nucleic acids, drug discovery, fabrication of miniature electronic, mechanic or other devices, and DNA based computation.

A. Nucleic Acid Analysis

The present invention provides an efficient means for fabricating high density polynucleotide arrays, which have been successfully employed in a variety of nucleic acid analysis applications. Polynucleotide arrays are useful in a variety of applications including but not limited to detecting specific mutations or polymorphisms and checking the accuracy and resolving ambiguity of previously elucidated sequences.

B. Gene Expression Monitoring

Polynucleotide arrays can be used for simultaneously monitoring the expression of multiple genes and eventually all genes as transcript sequences become available. Gene expression monitoring at the mRNA level can be carried out by extracting mRNA or total RNA from tissue or cell samples; fragmenting and labeling the RNA samples; hybridizing the fragmented RNA samples to polynucleotide arrays and detecting the hybridization pattern to determine quantitatively the level of specific mRNAs. Various levels of transcript processing, such as RNA splicing, can also be monitored using polynucleotide arrays. Specific embodiments for gene expression monitoring are disclosed in U.S. patent application Ser. No. 08/529,115, filed Sep. 15, 1995, and PCT Application No. PCT/US96/14839, filed Sep. 13, 1996, incorporated by reference herein in their entirety for all purposes.

The present invention is also used to immobilize nucleic acid sequences on a substrate. Immobilized nucleic acid sequences are used for various hybridization assays.

Hybridization of such immobilized nucleic acids with mRNA samples (or immobilized mRNA samples) is detected to monitor gene expression in some embodiments.

C. Drug Discovery

The significantly enhanced resolution made possible by the present invention permits the synthesis of more polymers on a given surface area. Therefore, the invention can be used for building chemical library and screening for biological activities of a large number of compounds in drug discovery using combinatorial chemistry.

D. DNA Computation

Polynucleotides have been used in DNA based computation. Spatially defined polynucleotide arrays are useful for certain DNA computation tasks. DNA computation employs the ligation, enzymatic cleavage and hybridization of polynucleotides. In some embodiments, polynucleotide arrays are used for accessing the result of DNA computation by detecting the presence of specific polynucleotides by specific hybridization. In some other embodiments, DNA computation is accomplished by manipulating polynucleotide arrays fabricated with chemical amplification.

Alternative Embodiments

According to other embodiments, spatially defined polymer synthesis will be performed by depositing a photoresist such as those used extensively in the semiconductor industry, more fully discussed in Ghandi, "VLSI Fabrication Principles," Wiley (1983) Chapter 10, incorporated herein by reference in its entirety for all purposes. According to these embodiments, a resist is deposited, selectively exposed, and etched, leaving a portion of the substrate exposed for coupling. These steps of depositing resist, selectively removing resist and monomer coupling are repeated to form polymers of desired sequence at desired locations.

In some specific embodiments, a positive-tone resist comprised of diazonapthoquinone-novolac (DNQ/N) is incorporated in a cresol-formaldehyde polymer matrix. This resist and its variants are used routinely in the microelectronics industry for submicron resolution lithography, as more fully discussed in Reiser, "Photoreactive Polymers: the Science and Technology of Resists", Wiley (1989), incorporated herein by reference in its entirety for all purposes. High contrast detritylation at a resolution of <4 microns has been demonstrated in simple contact printing experiments with this resist. Unfortunately, the alkaline conditions needed to develop the DNQ/N resists (aqueous [OH$^-$]>0.1 M) complicates its direct use in a multi-step polymer synthesis, such as the polynucleotide array fabrication process, because of the hydrolysis of akali-labile nucleobase protecting groups that are used to prevent side reactions during synthesis with standard phosphoramidite monomers using dimethoxytrityl (DMT) as a protecting group. A preferred embodiment uses alkali-resistant acid labile nucleobase protecting groups, such as monomethoxytrityl (MMT), and akali-labile 5' hydroxyl group to avoid this difficulty. MMT is completely resistant to the aqueous alkali developer, and readily removed with dilute acid post-synthesis. Alkali labile protection is used for the 5' hydroxyl group so that it will be susceptible to cleavage in the same alkaline solutions used for resist development, so that the two processes occur simultaneously. One preferred embodiment uses benzyol group as alkali-labile protection group because the benzyol group is sufficiently selective for the 5' hydroxyl group in preparing the monomer. More sterically hindered acyl protecting moieties, such as isobutyrl or pivaloyl, can also be used to enhance selectivity in monomer preparation.

EXAMPLE I

Removal of Protecting Groups by Acid Amplification

Efficient removal of protective groups as taught by the present invention is demonstrated in the following experiment.

A system using an ester of toluenesulfonic acid as a PAAC and an autocatalytic ester of pentafluorobenzoic acid (1,4-cyclohex-2-enediylbis-(pentafluorobenzoate)) as an enhancer was employed. An experiment was conducted to determine time and intensity required to achieve efficient deprotection.

The synthesis of 1,4-cyclohex-2-enediylbis-(pentafluorobenzoate) and 2-nitro-3,4-dimethoxybenzyl tosylate were carried out according to Houlihan et al., *Chemistry of Mat.* 3:462–471, 1991. The yields were 54% and 62%, respectively.

Solutions containing poly (methyl methacrylate) (PMMA, average molecular weight of 15,000 dalton) (14.0 wt %), 1,4-cyclohex-2-enediylbis-(pentafluorobenzoate) (7.0 wt %), and 2-nitro-3,4-dimethoxybenzyl tosylate (0.5, 0.8, 1.2, 1.6, or 2.3 wt %) in cyclohexanone were spin coated as ca. 1 μm thick films onto glass substrates bearing 5'-dimethoxytrityl (DMT) protected foundation molecules. In this case the surface of the glass substrate was reacted with DMT-hexaethyloxy-glycol-CE-phosphoramidite.

The resulting films were dried (prebaked) at 85° C. for 1 min. and then exposed with increasing doses of light (365–400 nm) from a collimated source (Oriel, Straford, Conn.) through a chrome on quartz mask in contact with the substrate. After exposure, the films were postbaked at 85° C. for 1 min. and stripped by rinsing with acetone (2 min.).

The free hydroxyl group was then reacted with a solution of Fluoreprime(c) fluorescein amidite in acetonitrile, using a modified Applied Biosystems Inc. (ABI) DNA synthesizer. The fluorescein amidite was coupled with the free hydroxyl groups, but not the DMT protected hydroxyl groups. The fluorescent output of the surface of the substrate was measured using a scanning fluorescence microscope. The coupling efficiency as measured by fluorescence intensity was used as a measurement of deprotection efficiency.

Another glass slide was deprotected with ethanolamine-ethanol (1:1 v/v, 30 min.) as complete deprotection control, the fluorescent output of the surface of the substrate was also measured using a scanning fluorescence microscope. The efficiency of deprotection was expressed in percentage of deprotection using the control slide as 100% deprotected.

Complete coupling occurred at low doses, ranging from 660 mJ/cm$^2$ to less than 33 mJ/cm$^2$. As shown in FIG. 1 the required exposure time was dependent on the amount of PAC in the substrate. When a formulation containing 0.02 g of PAC and 0.09 g of ester (enhancer) per 1 g of PMMA stock solution were used, the required exposure dose was 0.1 J/cm$^2$ corresponding to an exposure time of 3 seconds.

EXAMPLE II

High Resolution Synthesis of Polynucleotide and Hybridization with an Polynucleotide Probe Another important consideration for applying the techniques disclosed herein is whether the deprotection procedure interferes with the subsequent synthesis and functioning of the desired polymer arrays. The following experiment shows that functional polynucleotide arrays were synthesized by the method of the current invention.

A combination of a PAC and an enhancer in the form of a masked acid was used to synthese a standard checkerboard pattern of an polynucleotide on a glass slide. The resulting glass slide containing polynucleotide arrays was hybridized to a complementary polynucleotide probe to test resolution and integrity of the arrays.

Solutions containing poly (methyl methacrylate) (PMMA, average molecular weight 15,000) (14.0 wt %), 1,4-cyclohex-2-enediylbis(pentafluorobenzoate) (7.0 wt %), and 2-nitro-3,4-dimethoxybenzyl tosylate (1,2 wt %) in cyclohexanone were spin coated as approximately 1 μm thick films onto glass substrates bearing 5' dimethoxytrityl (DMT) protected foundation molecules.

The resulting films were dried (prebaking) at 85° C. for 1 min. and then exposed to light (0.2 J/cm2, 365–400 nm) from a collimated source (oriel) through a chrome on quartz mask in contact with the substrate.

After exposure, the films were postbaked at 85° C. for 1 min. and stripped by rinsing with acetone, ethanol, and acetone again (each rinse 2 min.). The free hydroxyl group was then reacted with a DMT protected nucleotide phosphoramidite in acetonitrile, using a modified Applied Biosystems Inc. (ABI) DNA synthesizer. This coat/expose/strip process was repeatedly used to build an polynucleotide of the sequence 5'-CATTTACAGC-3'.

The resulting polynucleotide was deprotected with ethanolamine—ethanol (1:1 v/v, 18 h) and then hybridized to a fluorescent labeled target containing the complementary sequence 5'-GCTGTAAATG-3'.

The high fluorescence intensity achieved, as observed with a scanning fluorescence microscope is a measurement of the combined efficiency of polynucleotide synthesis and hybridization. Yield of the polymer prepared using the method of invention was comparable to that of the standard MeNPoc VLSIPS method. Data showed a checkerboard pattern with a feature size of 10 μm. The high intensity of fluorescence also indicated a good fidelity of the synthesized polynucleotides, as demonstrated by the efficient hybridization of complementary probes to the arrays.

As shown in FIG. 2, resolution showing 5 μm and 2 μm lines were printed with the process of the present invention. A poly(ethylene glycol) linker molecule containing a DMT protected hydroxyl group was covalently bound to a substrate. The surface of the substrate was then coated with polymer containing a PAC and an enhancer, irradiated and heated as described above. The polymer film was then removed followed by reaction of the free hydroxyl groups with a biotin phosphoramidite. The image of FIG. 2 was obtained by incubating the substrate with a collodial gold label conjugated to strepavidin and detected using a Zeiss microscope with a CCD camera.

Figure 3:
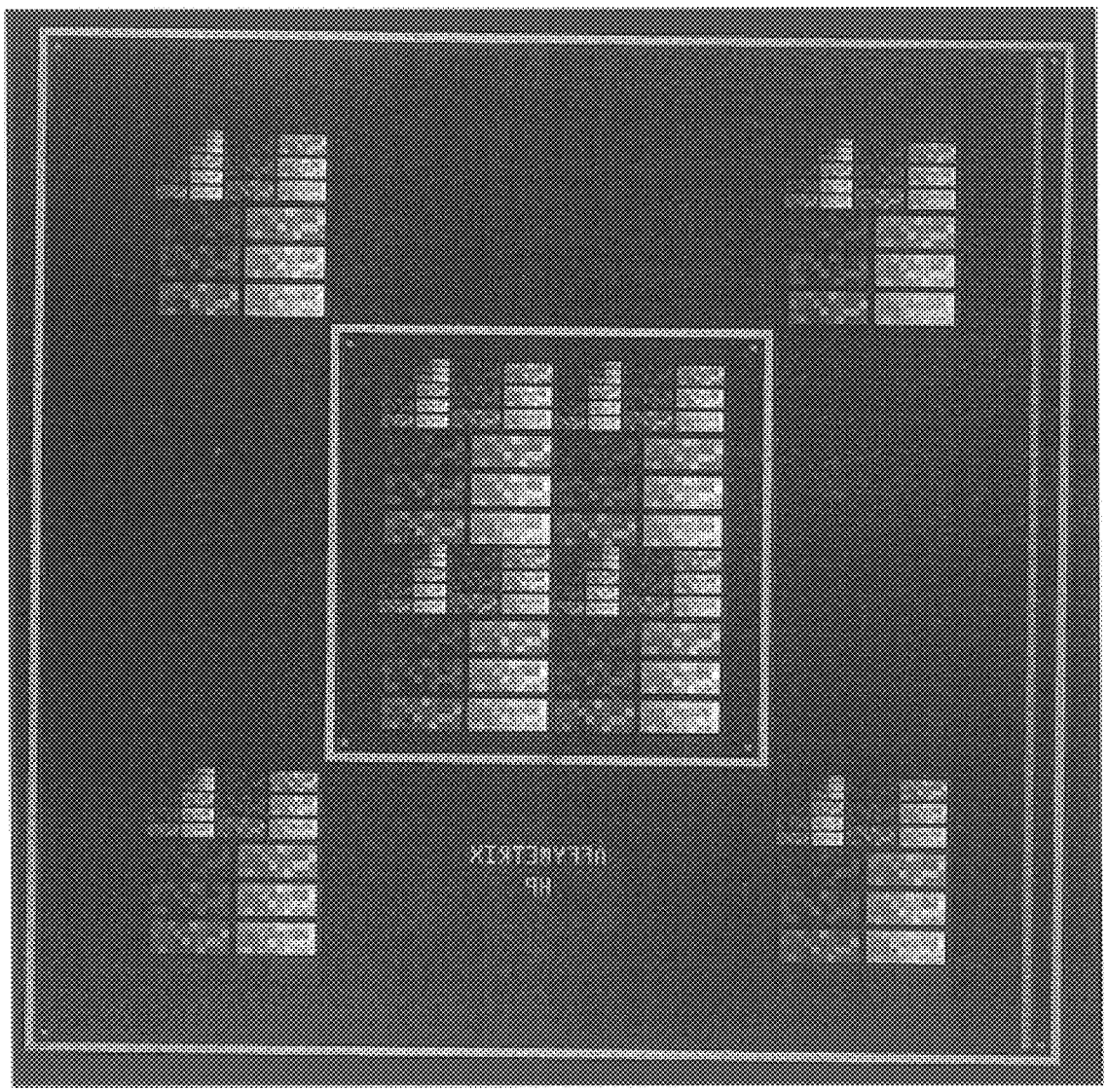
FIG. 3 is an array produced according to the method of the present invention.

As can be seen in FIG. 3, a fluorescent image of a probe array was made according to the teachings of the present invention. Probes vary from 10 to 20 bases in length and were prepared by repeating the synthesis steps, i.e. coating the substrate with e polymer containing a catalyst system, exposing the substrate to radiation to initiate a catalytic reaction to remove protective groups from reactive functional groups, stripping away the polymer layer and then adding a monomer to react with the free reactive group, on the order of thirty times. Feature sizes in FIG. 3 vary from 100 to 20 microns.

EXAMPLE III

Lithographic Evaluation

Figure 4:
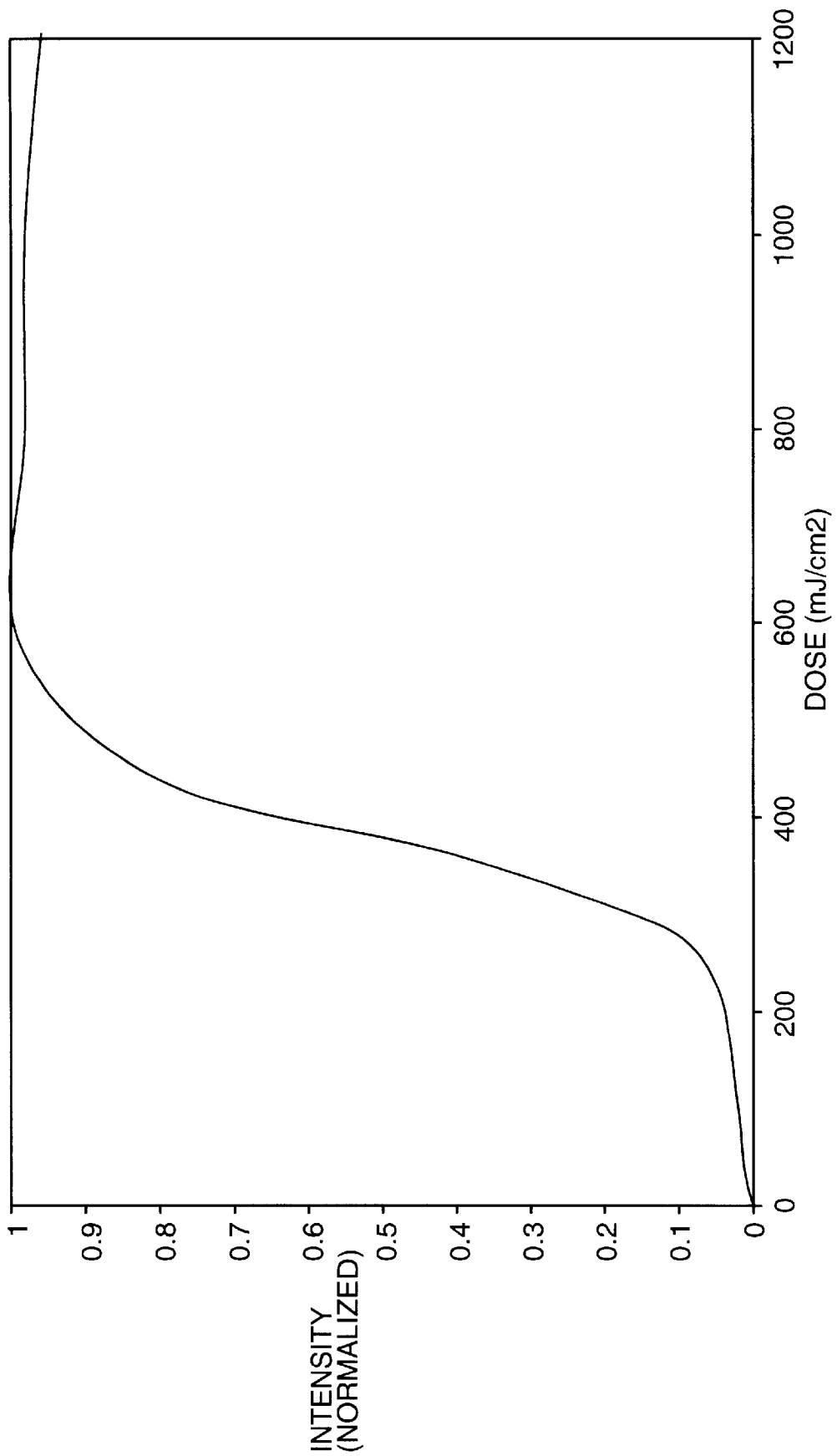
FIG. 4 is a graph showing the nonlinear behavior of the response as a function of the irradiation does.

As shown in FIG. 4, the high contrast observed in photo processes reflects the nonlinearity of the response as a function of the irradiation dose. In traditional photo resists, this nonlinearity stems from the solubility behavior of the polymer. Although the catalytic photo process described in this application does not involve a development step, nonlinear behavior was observed. This probably results from a titration effect: a quantity of acid must accumulate before the DMT group is removed.

The lithographic behavior of the process was evaluated by spin coating a 0.5 μm thick film of poly (methyl methacrylate) (PMMA) containing the nitrobenzyl ester PAC (0.5 wt %) and the enhancer (8 wt %) having the following structures:

Photo Activated Catalyst (PAC)

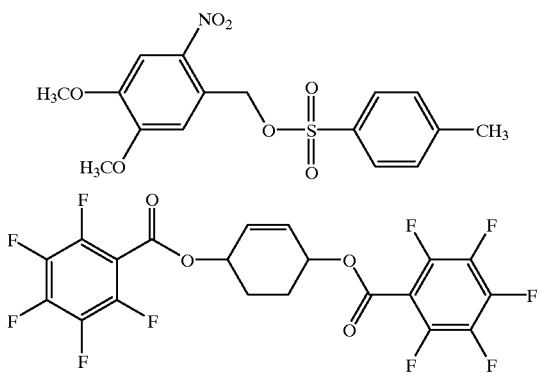

onto a glass substrate bearing covalently bound polynucleotides whose terminal 5' hydroxyl groups were DMT protected. The coated substrate was prebaked at 85° C. for 2 min, irradiated with varying doses at 365 nm, and postbaked at 85° C. for 2 min. The polymer coating was then removed with an acetone wash and the surface treated with a fluorescent coupling reagent. As shown by the sensitivity curve in FIG. 4, the lithographic process generated a direct image with a sensitivity of 600 mJ/cm$^2$ at 365 nm and a contrast of 3.0. By increasing the concentration of the PAC, the sensitivity of the system can be significantly improved. However, this may result in a decrease in the contrast. The contrast was calculated using the contrast equation as defined in Reiser, Arnost, Photoreactive Polymers: the Science and Technology of Resists, pp. 226–228 (1989), incorporated in its entirety herein by reference for all purposes.

Figure 5:
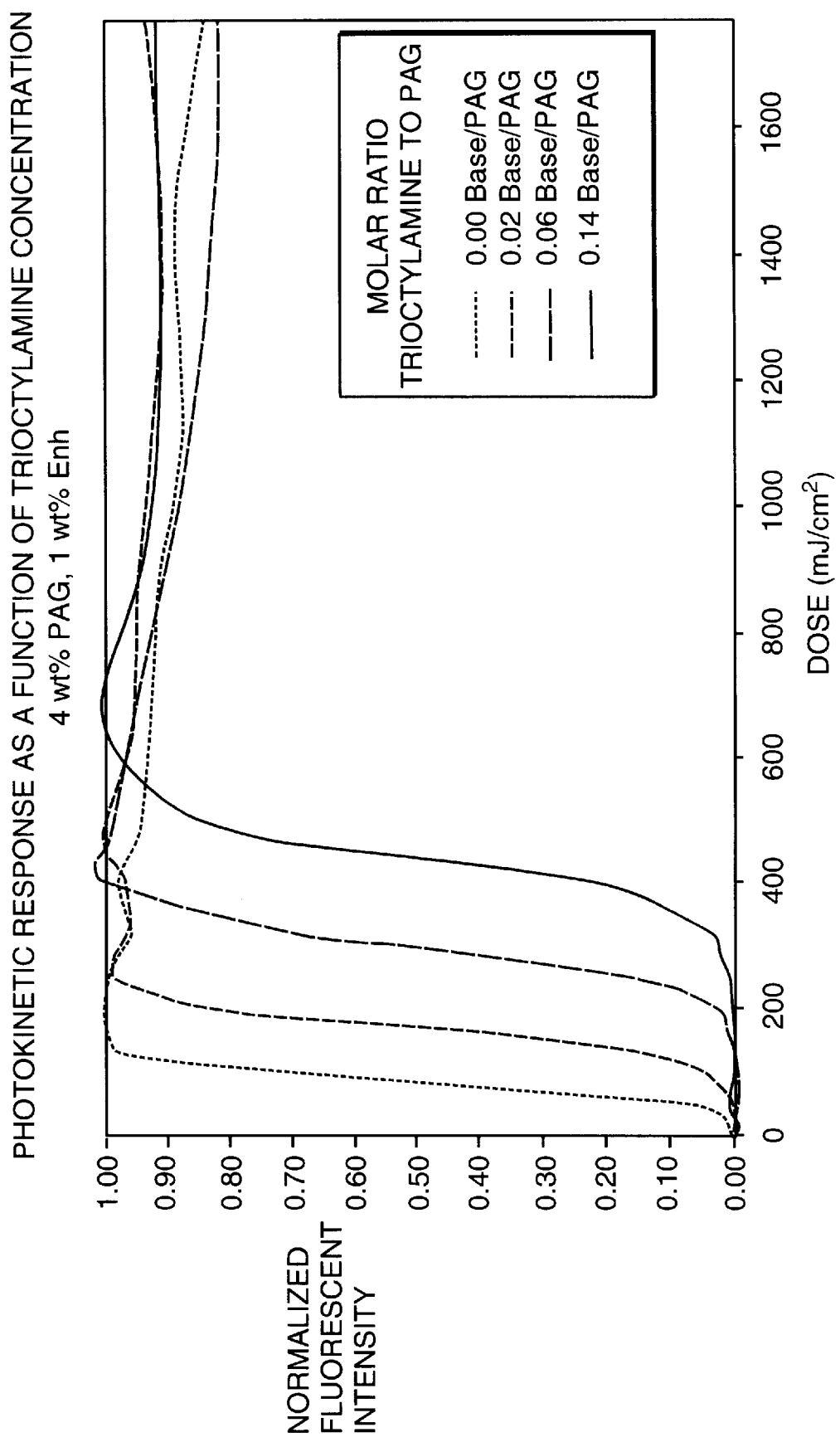
FIG. 5 is a graph of the photokinetic response as a function of trioctylamine concentration.

In addition to tuning the sensitivity and the contrast by altering the concentration of the PAC and the enhancer, it is also possible to affect these two properties by adding an amine to the formulation to improve environmental stability and resolution of the resist. Photokinetic response was measured as a function of the concentration of trioctylamine. As shown in FIG. 5, the dose required to reach complete detritylation increased with increasing concentrations of trioctylamine (increasing from 130, 240, 400, and 650 mJ/cm$^2$ for added base of 0.0, 0.08, 0.24 and 0.56 wt % respectively.

EXAMPLE IV

Coupling Efficiency in Polynucleotide Array Fabrication

We have used the chemically amplified photo process in conjunction with nucleoside phosphoramidite coupling chemistry to fabricate polynucleotides with mixed and unmixed sequences. By employing a cleavable linker and a fluorescent label (FL*label) at the 3' end of the sequence, the polynucleotide can be removed from the glass substrate and analyzed by HPLC. A typical probe sequence has the following construction (where B represents a nucleotide base):

SUBSTRATE—Linker—FL*Iabel—3'-BBBBBB5'—OH

After synthesis, the sequence was simultaneously cleaved from the surface and deprotected by soaking in ethanol/ethylenediamine (1:1 v/v) for 15 h at 25° C. The sequence was then directly analyzed using HPLC with an anion exchange column and a fluorescence detector. To compare the chemically amplified photo process to traditional polynucleotide chemistry, each probe sequence was synthesized twice: once using the chemically amplified photo process for the deprotection step and once using the traditional deprotecting reagent, 3% trichloroacetic acid in dichloromethane (TCA/DCM).

Figure 6:
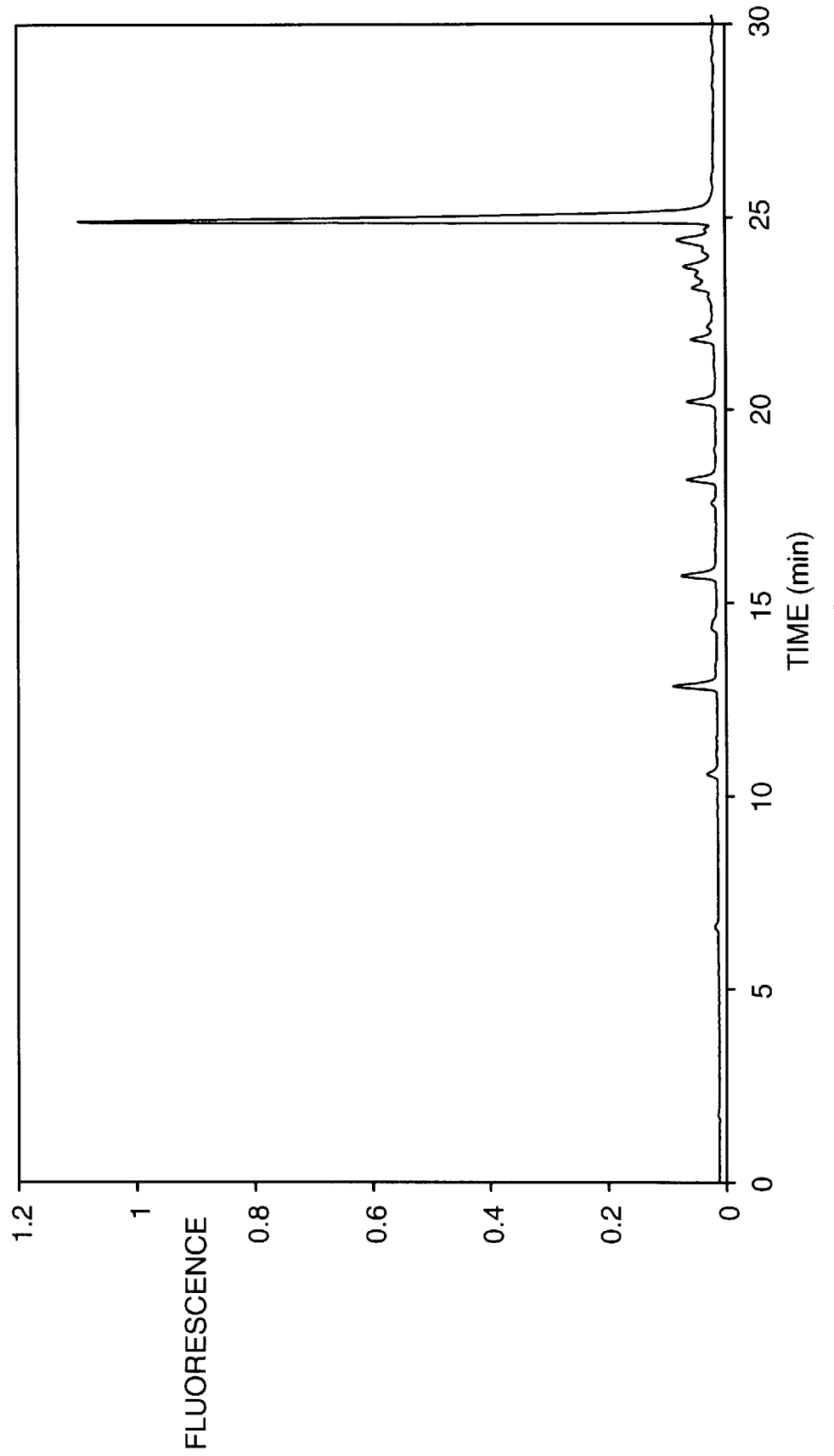
FIG. 6 is a chromatogram of a labeled $T_6$ polymer synthesized with the chemically amplified photo process.
Figure 7:
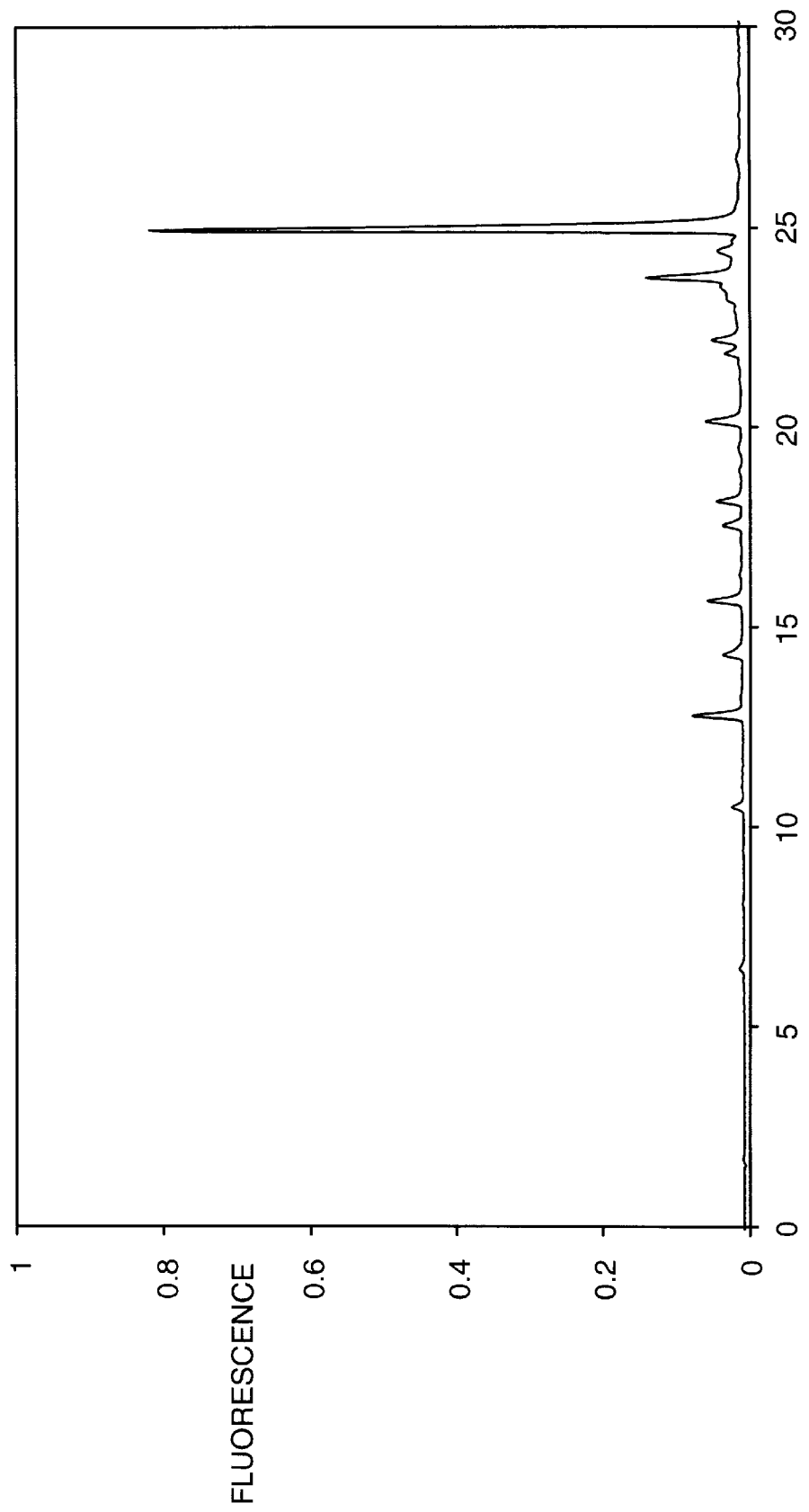
FIG. 7 is a chromatogram of a labeled $T_6$ polymer synthesized with TCA/DCM.

FIGS. 6 and 7 show the chromatograms of a labeled $T_6$ polymer synthesized with the chemically amplified photo process and TCA/DCM, respectively. The predominant peak at 21.7 min corresponds to the full length polymer, while the small peaks eluting earlier represent the shorter truncated polymers. The integration data showed that the yields for the full length polymer are 63% using the photo process and 80% using TCA/DCM, corresponding to a step wise efficiency of 93% and 96%, respectively. Further analyses of other sequences indicated that the step wise coupling efficiency for the photo process ranges from 90–96%, approaching the efficiencies achieved using TCA/DCM as the deprotecting reagent.

The present invention provides methods, compositions, and apparatus involving synthesis of polymers on substrates. It is to be understood that the embodiments of the present invention which have been described are merely illustrative of some applications of the principles of the invention. Numerous modifications may be made by those skilled in the art without departing from the true spirit and scope of the invention. By way of example, the invention has been described primarily with reference to the use of PAACs, catalytic compounds labile to acid-cleavage, such as acid thermolytic cleavage, and acid removable protective groups, but it will be readily recognized by those of skill in the art that photobases, base labile protective groups, and other systems involving chemical amplification can be used. It should be apparent to those of skill in the art that protecting groups can be the photocatalyst generator and can undergo autocatalytic reactions. It should also be readily recognized by those of skill in the art that sources of radiation other than light could be used. For example, in some embodiments, it may be desirable to use initial compounds for generating catalysts or acids which are sensitive to electron beam irradiation, x-ray irradiation, in combination with electron beam lithography, or x-ray lithography techniques. The scope of the invention should, therefore, be determined not with reference to the above description, but should instead be determined with reference to the appended claims, along with the full scope of equivalents to which such claims are entitled.

All of the references cited in this application are incorporated herein by reference in their entirety for all purposes even if not listed as such anywhere else in this application.

What is claimed is:

1. An apparatus for solid phase chemical synthesis comprising:
   i) a substrate having one or more synthesis intermediates bound thereon, the one or more synthesis intermediates including a reactive group protected from reaction by a removable protecting group attached by a chemical bond to the one or more synthesis intermediates;
   ii) a radiation sensitive compound or group, said radiation sensitive compound or group producing a catalyst when irradiated, and
   iii) an autocatalytic compound or group, said autocatalytic compound or group generating a protecting group removing product when said autocatalytic compound is activated by said catalyst,
   wherein the radiation sensitive compound or group and the autocatalytic compound or group are included in a polymer layer on the substrate and further wherein the radiation sensitive compound or group and the autocatalytic compound or group are nonidentical and wherein the catalyst and autocatalytic compound or group are nonidentical.

2. The apparatus recited in claim 1 wherein said radiation sensitive compound is a photosensitive compound.

3. The apparatus recited in claim 1 wherein said autocatalytic compound is a masked acid.

4. The apparatus recited in claim 1 wherein said synthesis intermediate is a linker molecule.

5. The apparatus recited in claim 1 wherein said synthesis intermediate is a nucleotide.

6. The apparatus recited in claim 1 wherein said synthesis intermediate is an polynucleotide.

7. The apparatus recited in claim 1 wherein said synthesis intermediate is an amino acid.

8. The apparatus recited in claim 1 wherein said synthesis intermediate is an polypeptide.

9. The apparatus recited in claim 1 wherein said removable protecting group is an acid removable group.

10. The apparatus recited in claim 1 wherein said autocatalytic compound is pentafluorobenoic acid.

11. The apparatus recited in claim 1 wherein said acid removable protecting group is 5' dimethoxytrityl.

12. The apparatus of claim 1 wherein the protecting group is selected from the group consisting of dimethoxytrityl (DMT), tert-butylcarbamate (tBoc), trifluoroacetyl (Tfa), 9-fluorenylmethoxycarbonyl (Fmoc), isobutyrl (iBu), benzoyl (Bz), phenoxyacetyl (pac), acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyl, tert-butyloxycarbonyl, 1-carbobenzoxamido-2,2,2-trifluoroethyl, 2,6-dichlorobenzyl, 2-(3,5-dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester.

13. The apparatus recited in claim 2 wherein said photosensitive compound is a photoactivated acid catalyst.

14. The apparatus recited in claim 2 wherein said photosensitive compound is a photoactivated catalyst.

15. The apparatus recited in claim 14 wherein said photoactivated catalyst is toluenesulfonic acid.

16. The apparatus of claim 14 wherein the photoactivated catalyst is a member selected from the group consisting of naphthoquinone diazide sulfonic acids, 2,1,4-diazonaphthoquinone sulfonic acid esters, 2,1,5-diazonaphthoquinone sulfonic acid esters, nitrobenzyl esters, s-triazine derivatives of nitrobenzyl esters, 1,1-bis(p-chorophenyl)-2,2,2-trichloroethane (DDT), 1,1-bis(p-methoxyphenyl)-2,2,2-trichloroethane, 1,2,5,6,9,10-hexabromocyclododecane, 1,10-dibromodecane, 1,1-bis(p-chlorophenyl)-2,2-dichloroethane, 4,4 dichloro-2-(trichloromethyl) benzhydrol (Kelthane), hexachlorodimethyl sulfone, 2-chloro-6-(trichloromethyl) pyridine, o,o-diethyl-o-(3,5,6-trichloro-2-pyridyl) phosphorothionate, 1,2,3,4,5,6-hexachlorocyclohexane, N(1,1-bis(p-chlorophenyl)-2,2,2-trichloroethyl)acetamide, tris (2,3-dibromopropyl) isocyanurate, 2,2-bis(p-chlorophenyl-1,1-dichloroethylene, tris (trichloromethyl) striazine, 1,1-bis(chlorophenyl)-2,2,2-trichloroethanol, tris (1,2,3-methanesulfonyl) benzene, tris(trichloromethyl) trizine, onium salts, diaryl-diazonium salts, onium salts of group VI and VII of the Periodic Table, halonium salts, quaternary ammonium, phosphonium and arsonium salts, aromatic sulfonium salts, sulfoxonium salts, seleonium salts, sulfonated esters, sulfonyloxy ketones, benzoin tosylate, t-butylphenyl alpha-(ptoluenesulfonyloxy)-acetate, t-butyl alpha-(p-toluenesulfonyloxy)-acetate, di-tert-butylphenyl iodonium triflate (TBI-T), di-tertbutylphenliodonium camphorsulfonate (TBI-CAM), di-tert-butylphenyl iodonium dichloracetate (TBI-DCA), naphthalimidotriftete, phthalimidotosylate, o-nitrobenzyl esters of toluenesulfonic acid, 2-nitro-3,4-dimethoxybenzyl tosylate,

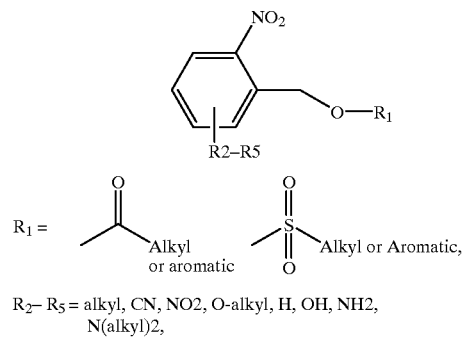

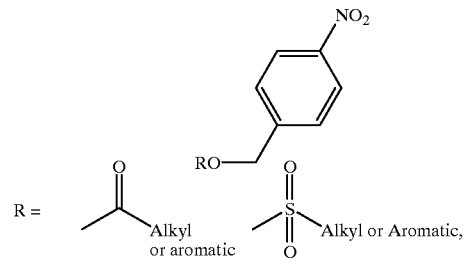

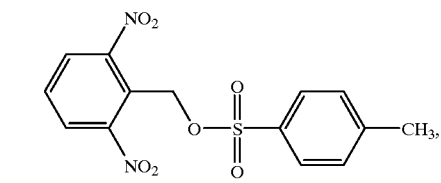

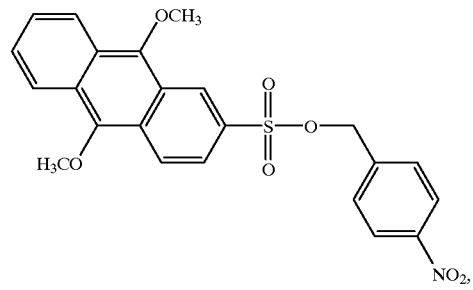

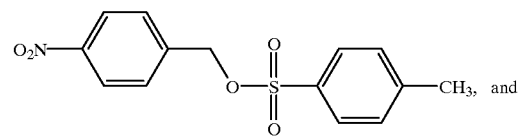

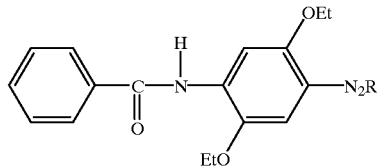

wherein R is sulfonate, tosylate, mesolate, PF$_6^-$ or BF$_4^-$.

wherein R is sulfonate, tosylate, mesolate, PF$_6^-$ or BF$_4^-$.

17. A substrate for use in making a polymer array comprising:
   a) a substrate having one or more synthesis intermediates bound thereon, the one or more synthesis intermediates having a reactive group protected from reaction by a protective group attached by a chemical bond to the one or more synthesis intermediates;
   b) a catalyst system for catalyzing removal of the protective group, the catalyst system contacting the synthesis intermediates and
   wherein the catalyst system is included in a polymer layer on the substrate and further wherein the catalyst system and the protective group are nonidentical.

18. A method of making a substrate for use in making a polymer array comprising:
   a) providing a substrate surface having one or more synthesis intermediates bound thereon, the one or more synthesis intermediates having a reactive group protected from reaction by a protective group attached by a chemical bond to the one or more synthesis intermediates;
   b) applying over the substrate surface a polymer layer having a catalyst system capable of catalyzing removal of the protective group.

* * * * *